United States Patent [19]

Gavrev et al.

[11] 4,187,725

[45] Feb. 12, 1980

[54] METHOD FOR ULTRASONIC INSPECTION OF MATERIALS AND DEVICE FOR EFFECTING SAME

[75] Inventors: Valery S. Gavrev; Jury M. Goncharuk; Sergei B. Birjukov; Alexandr V. Savitsky; Ljudmila A. Popova, all of Kishinev, U.S.S.R.

[73] Assignee: Vsesojuzny Nauchno-Issledovatelsky Institut Po Razrabotke Nerazrushajuschikh Metodov I Sredsv Kon-trolya Kachestva Materialov, Kishinev, U.S.S.R.

[21] Appl. No.: 922,585

[22] Filed: Jul. 6, 1978

[51] Int. Cl.$^2$ .............................................. G01N 29/04
[52] U.S. Cl. ....................................................... 73/613
[58] Field of Search .................. 73/613, 609, 610, 611, 73/612, 614, 615

[56] References Cited

U.S. PATENT DOCUMENTS

| 3,690,156 | 9/1972 | Robinson | 73/613 |
| 3,733,891 | 5/1973 | Weighart | 73/610 |

FOREIGN PATENT DOCUMENTS 568011  8/1977  U.S.S.R. .................................... 73/613

Primary Examiner—Stephen A. Kreitman
Attorney, Agent, or Firm—Haseltine, Lake & Waters

[57] ABSTRACT

According to the proposed method for ultrasonic inspection of materials, a reception and processing of ultrasonic vibrations reflected from a material being tested are followed by separating signals from noise at a preset level, which is carried out by means of time selection of signals performed within time intervals during which the signals' amplitudes exceed the preset level. In the device for effecting the method of this invention, an output of an ultrasonic generator, whose input is connected to one of the outputs of a synchronizer, is connected to an input of an ultrasonic converter acoustically coupled to the material being tested. An output of the ultrasonic converter is connected to an input of a reflected ultrasonic vibrations preprocessing unit whose output is electrically coupled to one of inputs of a signals recording unit. The coupling is effected either via a high-frequency amplifier, a no-noise-cutoff detector and a unit for separating signals from noise at a preset level, which are placed in series, or via the unit for separating signals from noise at a preset level, the high-frequency amplifier and the no-noise-cutoff detector placed in series. The unit for separating signals from noise at a preset level contains a gate pulse forming circuit and an AND circuit whose first input is electrically coupled to an input of the gate pulse forming circuit, the latter's output being connected to a second input of the AND circuit.

5 Claims, 7 Drawing Figures

METHOD FOR ULTRASONIC INSPECTION OF MATERIALS AND DEVICE FOR EFFECTING SAME

FIELD OF THE INVENTION

The present invention relates to methods and devices for nondestructive inspection of materials and, more particularly, to a method and device for ultrasonic inspection of materials.

The method and device of this invention are chiefly applicable to instruments and devices used for ultrasonic inspection of products and materials in metallurgy, as well as machine-building, power and aircraft industries. The invention is also applicable to information and measuring systems where pulse signals are used as data carriers.

BACKGROUND OF THE INVENTION

There is known a method for ultrasonic inspection of materials (cf. A. K. Gurvich, I. N. Yermolov, "Ultrazvukovoy control svarnych Shvov" /"Ultrasonic Inspection of Welds"/, Technika Publishers, Kiev, 1972, pp. 66-69), which consists in transmitting ultrasonic vibrations into a material, receiving and processing reflected ultrasonic vibrations, separating signals from noise at a present level, and assessing the sizes of flaws.

According to the method under review, the separation of signals from noise at a preset level (cutting off) is effected by limiting signals to a minimum; the present noise cutoff level must be acceptable for practical purposes.

A major disadvantage of the method under review is a distortion of the ratios between signals' amplitudes due to cutting off noise; as a result, it is absolutely impossible to make a correct quantitative evaluation of the sizes of flaws, which is normally done by comparing the amplitudes of signals reflected from a flaw with the amplitude of signals arriving from a reference reflector or the bottom surface of the material being tested.

The method under review is further disadvantageous in that the separation of signals from noise affects the sensitivity of flaw detection because the noise cutoff reduces the absolute values of signals' amplitudes.

There is known a device for ultrasonic inspection of materials, intended for carrying out the foregoing method. In this device, an output of an ultrasonic generator, whose input is connected to one of the outputs of a synchronizer, is connected to an input of an ultrasonic converter which is acoustically coupled to a material being tested; an output of the ultrasonic converter is electrically coupled via a reflected ultrasonic vibrations preprocessing unit and a high-frequency amplifier, which are placed in series, to an input of a unit for separating signals from noise at a preset level, the latter unit's output being connected to one of inputs of a signals recording unit whose other input is connected to a second output of the synchronizer.

In the device under review, the unit for separating signals from noise at a preset level comprises a noise-cutoff detector built around semiconductor diodes; the noise cutoff level is determined by the magnitude of reference voltage set by the operator.

The device has all the disadvantages inherent in the method it is intended to effect: distortion of the initial ratios between signals' amplitudes and lower flaw detection sensitivity due to the noise cutoff. Let it be assumed, for example, that the amplitudes of two signals received at the output of the preprocessing unit are 5 V and 25 V, respectively, and that the level, at which noise is cut off by the detector, is 3 V. Then, the ratio between the amplitudes after cutting off is (5-3): (25-3)=1:11, the true ratio being 1:5.

Thus, cutting off noises produces different effects upon the amplitudes of signals and changes the initial ratio between these amplitudes, wherefore it is impossible to assess correctly the sizes of flaws.

In order to establish the size of a flaw, one must first discontinue cutting off noise, whereupon the amplitudes of signals are measured and compared against the background of noise.

Naturally, this affects the accuracy of evaluating the sizes of flaws, as well as the sensitivity of the method.

Besides, in the case of automatic inspection, one must stop the inspection in order to measure and compare the amplitudes of signals so as to determine the sizes of flaws; as a result, the rate of inspection is reduced.

Another disadvantage of the device under review resides in the fact that cutting off noise narrows the dynamic range; this, in turn, is due to the fact that after cutting off noise, the gain factor of the receiving channel must be increased so as to ensure effective recording of signals. For example, a noise cutoff, which amounts to 60 percent of the height of the screen of the recording unit's cathode ray tube, halves the dynamic range of the device.

The decrease in absolute values of signals' amplitudes, due to cutting off noise, reduces the reliability of automatic recording of test results.

Besides, the device under review has a low resolution when detecting flaws which are close to one another in both in longitudinal and transverse directions; this equally applies to cases of a low signal-to-noise ratio and may be a serious disadvantage when checking some recently developed alloys which feature a relatively high structural noise level.

There is known another method for ultrasonic inspection of materials (cf. USSR Inventor's Certificate No. 219,639, Cl. G01 n 29/04), whereby ultrasonic vibrations are transmitted into a material being tested, whereupon the reflected ultrasonic vibrations are received and processed, signals are separated from noise at a preset level, and the sizes of flaws are assessed.

According to the latter method, the separation of signals from noise (the cutoff of noise) is carried out after adding together signals against the background of noise and signals whose level is reduced to a minimum, i.e. after raising the signal-to-noise ratio.

This method, too, does not rule out a change in the initial ratio of signals' amplitude because of cutting off noise, whereby it is impossible to make a correct quantitative evaluation of the sizes of flaws.

True, the reduction in the sensitivity is not as pronounced in the latter method as in the former one, because noise is cut off after the signal-to-noise ratio is improved in advance. However, this method is not effective enough at low signal-to-noise ratios, i.e. when flaws of small sizes have to be dealt with.

The foregoing method is carried out with the use of a device, wherein an output of an ultrasonic generator, whose input is connected to one of outputs of a synchronizer, is connected to an input of an ultrasonic converter which is acoustically coupled to a material being tested. An output of the ultrasonic converter is electrically coupled to one of inputs of a signals recording unit whose other input is connected to a second output of the synchronizer; the electrical coupling is effected via serially placed units which include a reflected ultrasonic vibrations preprocessing unit, a high-frequency amplifier, a no-noise-cutoff detector, and a unit for separating signals from noise at a preset level.

In the above device, the unit for separating signals from noise at a preset level comprises a noise cutoff detector, an adder and a noise cutoff circuit.

An input of the noise cutoff detector is connected to an output of the high-frequency amplifier and an input of the no-noise-cutoff detector; an output of the noise cutoff detector is connected to one of inputs of the adder whose second input is connected to an output of the no-noise-cutoff detector. The adder's output is electrically coupled via the circuit for cutting off noise at a preset level to one of inputs of the signals recording unit. The noise cutoff level is set by the operator and is determined by the magnitude of reference voltage of the noise cutoff detector and the noise cutoff circuit.

The latter device has all the disadvantages typical of the former device. First of all, it alters the initial ratios between the amplitudes of signals and has a low sensitivity when defecting flaws of small dimensions.

Secondly, in the case of automatic inspection the device makes it necessary to stop the inspection in order to evaluate the dimensions of flaws, whereby the rate of inspection is sharply reduced.

Thirdly, the separation of signals from noise at a preset level narrows the dynamic range of the device.

In the fourth place, the device does not provide for reliable automatic recording of signals reflected from small-size flaws when operating at a high noise level.

Finally, the device has a low resolution when inspecting articles manufactured from materials featuring a high level of structural noise.

SUMMARY OF THE INVENTION

In view of the above, it is an object of the present invention to maintain the initial amplitudes of signals and the initial ratios between them, while cutting off noise.

It is a further object of the invention to improve the sensitivity of flaw detection.

It is a further object of the invention to improve the confidence of inspection.

Another important object of the invention is to improve the resolution of ultrasonic flaw detectors while testing materials featuring a high level of structural noise.

It is a further object of the invention to provide for detection and automatic recording of signals reflected from flaws of small dimensions at high noise levels.

It is one of the major objects of the invention to accelerate the rate of ultrasonic inspection of materials.

Finally, it is an object of the invention to maintain the dynamic range of ultrasonic flaw detectors while separating signals from noise at a preset level.

The foregoing objects are attained by providing a method for ultrasonic inspection of materials, according to which ultrasonic vibrations are transmitted into a material being tested, whereupon they are received and processed, signals are separated from noise at a preset level, and the dimensions of flaws are established, which method is characterized by that the separation of signals from noise is effected by means of time selection of signals performed within time intervals during which the amplitudes of signals exceed a predetermined noise level.

The objects of this invention are further attained by providing a device for carrying out the proposed method for ultrasonic inspection of materials, wherein an output of an ultrasonic generator, whose input is connected to one of outputs of a synchronizer, is connected to an input of an ultrasonic converter which is acoustically coupled to a material being tested, an output of the ultrasonic converter being electrically coupled via a reflected ultrasonic vibrations preprocessing unit, as well as via a no-noise-cutoff detector with a high-frequency amplifier at its input and a unit for separating signals from noise at a preset level, which are placed in series, to one of the inputs of a signal recording unit whose other input is connected to a second output of the synchronizer, which device is characterized, according to the invention, by that the unit for separating signals from noise at a preset level comprises a gate pulse forming circuit and an AND circuit whose first input is electrically coupled to an input of the gate pulse forming circuit, while the latter's output is connected to a second input of the AND circuit.

It is expedient that the input of the high-frequency amplifier should be connected to the output of the reflected ultrasonic vibrations preprocessing unit, that the output of the no-noise-cutoff detector should be electrically coupled to the input of the gate pulse forming circuit, and that the output of the AND circuit should be connected to one of the inputs of the signals recording unit.

It is further expedient that the input of the gate pulse forming circuit should be electrically coupled to the output of the reflected ultrasonic vibrations preprocessing unit, that the output of the AND circuit should be connected to the input of the high-frequency amplifier, and that the output of the no-noise-cutoff detector should be connected to one of the inputs of the signals recording unit.

It is equally expedient that the unit for separating signals from noise at a preset level should additionally include a delay circuit, its output being connected to the first input of the AND circuit, while its input is connected to the input of the gate pulse forming circuit.

It is expedient that the input of the delay circuit should be connected to the output of the no-noise-cutoff detector.

It is equally expedient that the input of the delay circuit should be connected to the output of the reflected ultrasonic signals preprocessing unit.

The method for ultrasonic inspection of materials according to the invention and the proposed device for carrying out this method make it possible to keep intact the initial amplitudes of signals, as well as the initial ratios between these amplitudes, while cutting off noise, which, in turn, provides for a correct quantitative evaluation of dimensions of flaws in materials being tested, as well as a high sensitivity, reliability, resolution and a broad dynamic range of the device, in combination with a high rate of inspection.

BRIEF DESCRIPTION OF THE ATTACHED DRAWINGS

Other objects and advantages of the present invention will become more apparent from the following detailed description of preferred embodiments thereof to be read in conjunction with the accompanying drawings, wherein.

Figure 1:
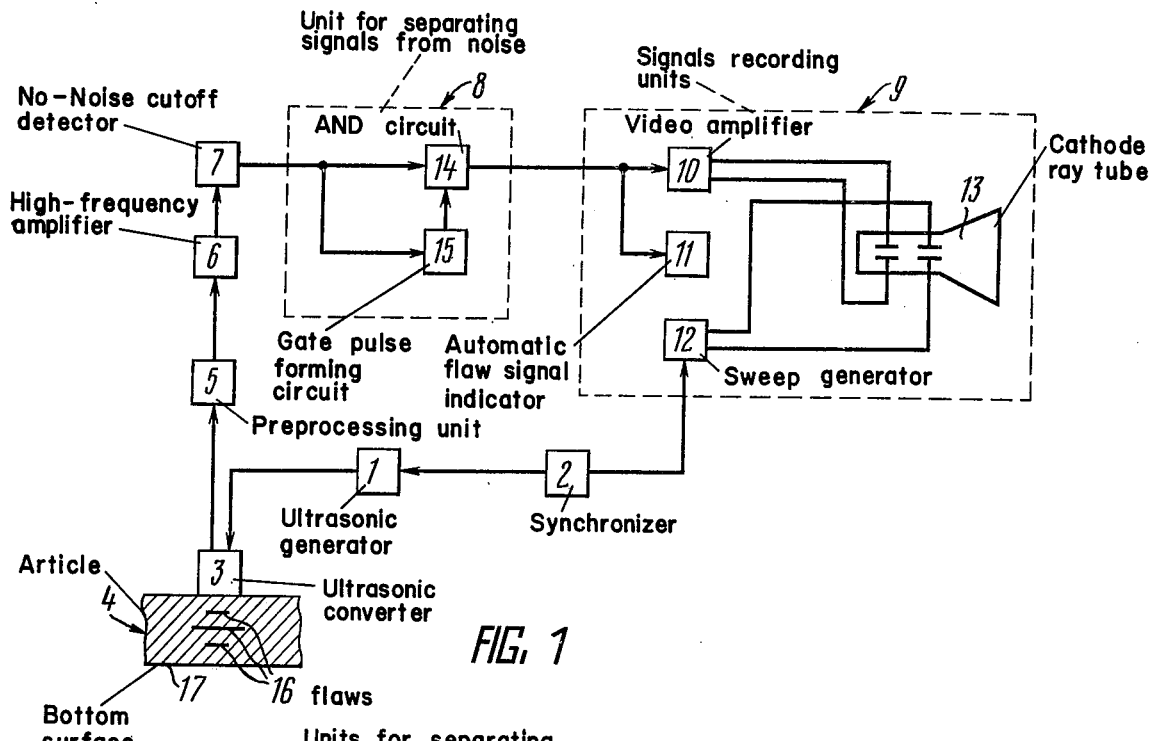
FIG. 1 is a block diagram of a device for ultrasonic inspection of materials in accordance with the invention, comprising a no-noise-cutoff detector and a unit for separating signals from noise at a preset level, placed in series.
Figure 5A:
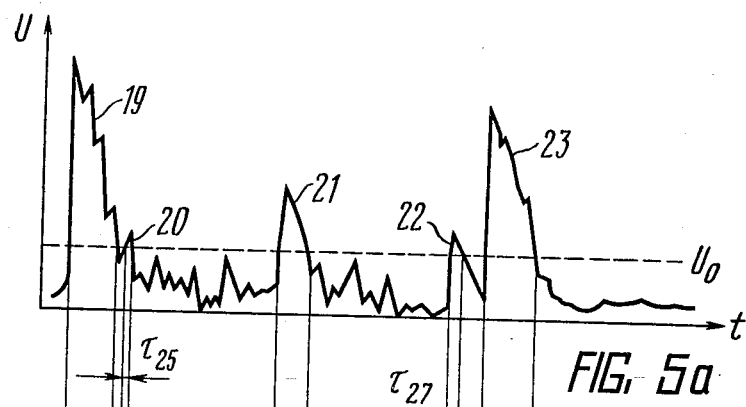

FIGS. 5a, b and c are time plots illustrating processes taking place at different points of the device for ultrasonic inspection of materials according to the invention, presented in FIG. 1.

DETAILED DESCRIPTION OF THE INVENTION

The proposed method for ultrasonic inspection of materials is as follows.

Ultrasonic vibrations are transmitted into the material of a product being tested and are received as they are reflected from flaws and the bottom surface of the product. The reflected vibrations are then preprocessed, i.e. amplified and detected, and signals are separated from noise at a preset level. The signals thus separated include the main bang and pulses reflected from flaws and the bottom surface of the product being tested.

The separation of signals from noise at a level is acceptable for practical purposes is effected by means of time selection of signals, performed within time intervals during which the signals' amplitudes exceed a predetermined noise level.

The proposed device for effecting the method for ultrasonic inspection in accordance with the invention comprises an ultrasonic generator 1 (FIG. 1) and a synchronizer 2 which is a blocking generator one of whose outputs is connected to an input of the ultrasonic generator 1.

The latter's output is connected to an input of an ultrasonic converter 3 acoustically coupled to the material of an article 4 being tested, which is shown in section.

Through a reflected ultrasonic vibrations preprocessing unit 5, a high-frequency amplifier 6, a no-noise-cutoff detector 7 and a unit 8 for separating signals from noise at a preset level, an output of the ultrasonic converter 3 is electrically coupled to one of inputs of a signals recording unit 9.

The reflected ultrasonic vibrations preprocessing unit 5 is a time-varied gain control preamplifier.

The signals recording unit 9 includes a video amplifier 10 and an automatic flaw signal indicator 11. Inputs of the video amplifier 10 and indicator 11 are connected to an output of the unit 8 for separating signals from noise at a preset level. The signals recording unit 9 further includes a sweep generator 12, whose input is connected to another output of the synchronizer 2, and a cathode ray tube 13. Outputs of the video amplifier 10 and sweep generator 12 are connected to vertical- and horizontal-deflection plates, respectively, of the cathode ray tube 13.

According to the invention, the unit 8 for separating signals from noise at a preset level comprises an AND circuit 14 whose output is connected to the inputs of the video amplifier 10 and the automatic flaw signal indicator 11; the unit 8 further includes a gate pulse forming circuit 15 which is a threshold element with an adjustable trigger level, whose input is connected to a first input of the AND circuit 14 and to an output of the no-noise-cutoff detector 7. An output of the gate pulse forming circuit 15 is connected to a second input of the AND circuit 14.

FIG. 1 conventionally shows flaws 16 and a bottom surface 17 of the article 4 being tested.

Figure 2:
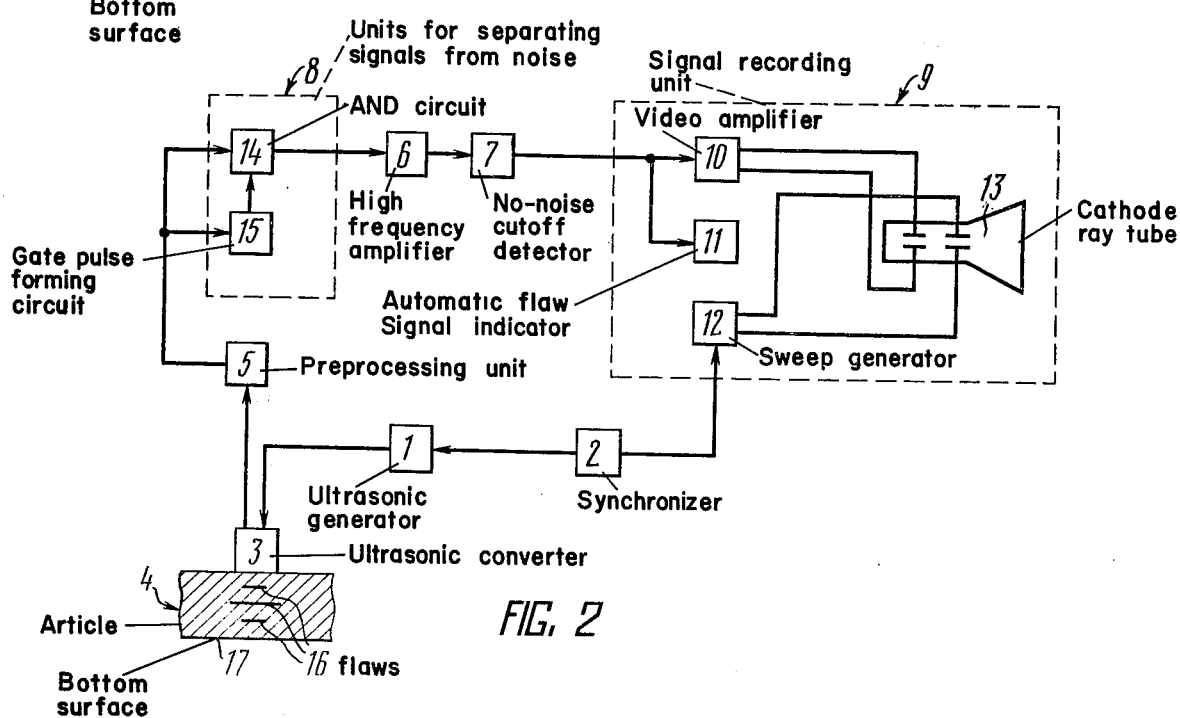
FIG. 2 is a block diagram of a device for ultrasonic inspection of materials in accordance with the invention, comprising a unit for separating signals from noise at a preset level, a high-frequency amplifier and a no-noise-cutoff detector, placed in series.

Unlike the device of FIG. 1, the device of FIG. 2 has the output of reflected ultrasonic vibrations preprocessing unit 5 (FIG. 2) electrically coupled to one of the inputs of the signals recording unit 9, the coupling being effected through the unit 8 for separating signals from noise at a preset level, the high-frequency amplifier 6 and the no-noise-cutoff detector 7 which are placed in series. In the unit 8 for separating signals from noise at a preset level, the first input of the AND circuit 14 and the input of the gate pulse forming circuit 15 are connected to the output of the reflected ultrasonic vibrations preprocessing unit 5; the output of the AND circuit 14 is connected to the input of the high-frequency amplifier 6.

Figure 3:
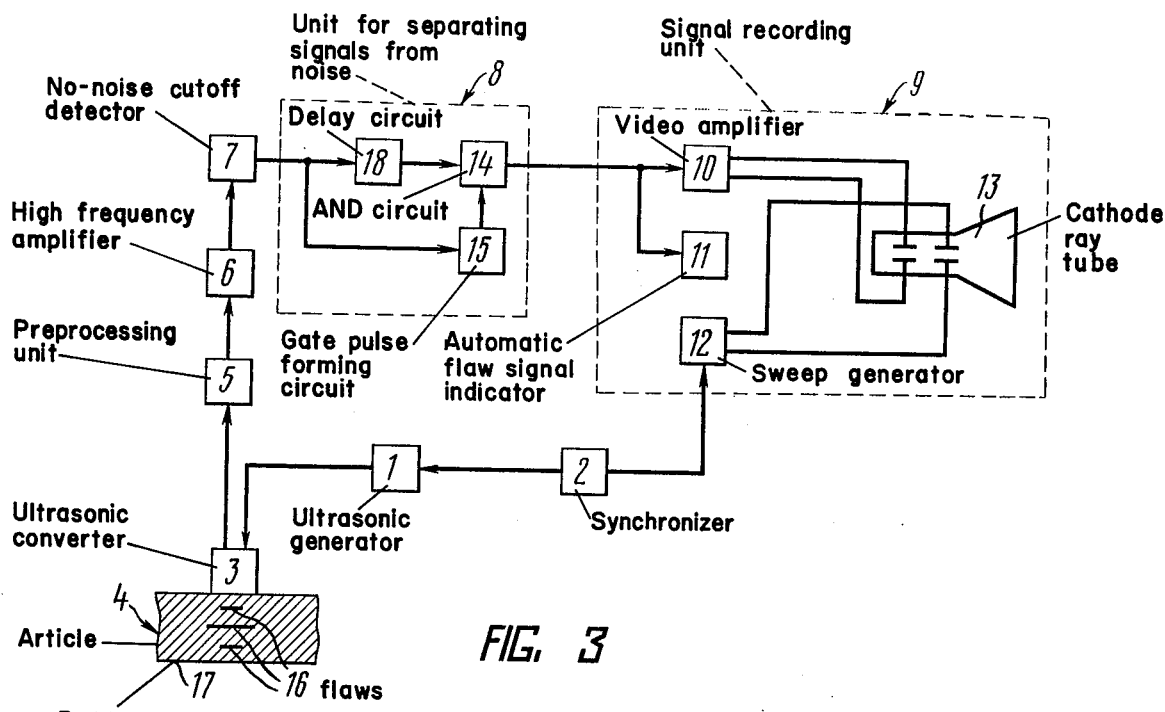
FIG. 3 is a block diagram of the device of FIG. 1, provided with a delay circuit in accordance with the invention.

Unlike the device of FIG. 1, the unit 8 (FIG. 3) for separating signals from noise at a preset level of the device shown in FIG. 3 additionally includes a delay circuit 18 whose output is connected to the first input of the AND circuit 14. The input of the gate pulse forming circuit 15 is connected to an input of the delay circuit 18 and to the output of the no-noise-cutoff detector 7.

Figure 4:
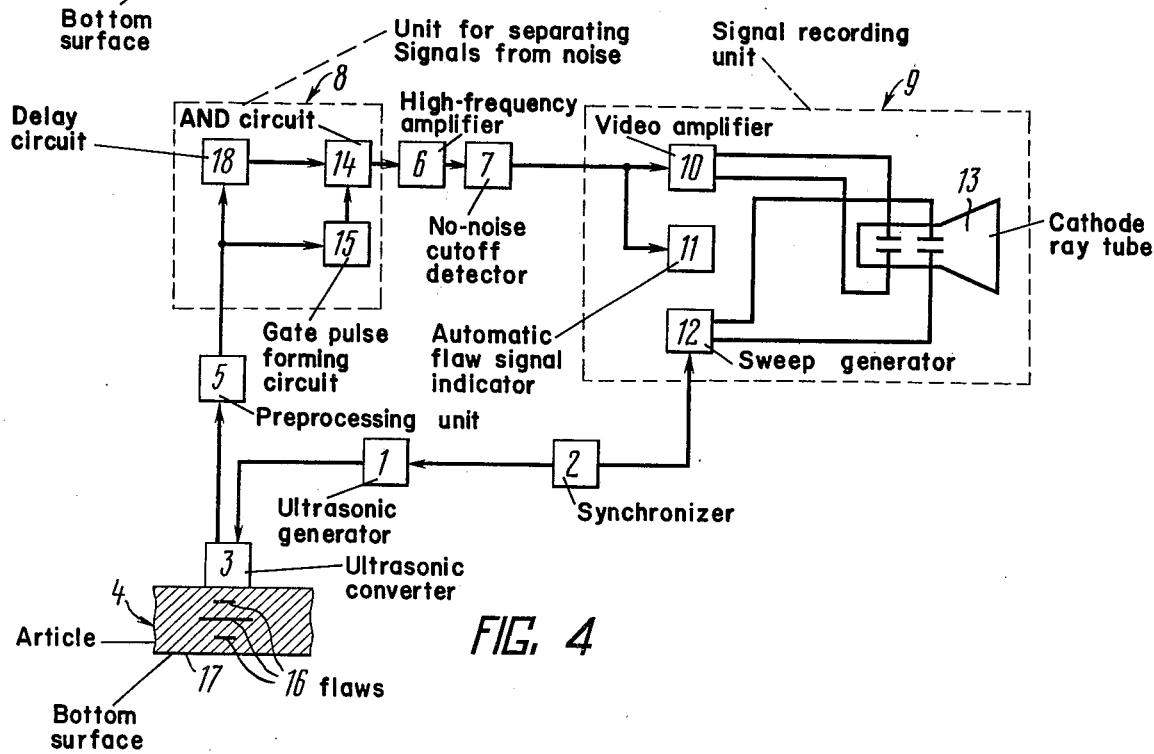
FIG. 4 is a block diagram of the device of FIG. 2, provided with a delay circuit in accordance with the invention.

Unlike the device of FIG. 2, in the device of FIG. 4, the unit 8 (FIG. 4) for separating signals from noise additionally includes the delay circuit 18 whose output is connected to the first input of the AND circuit 14. The input of the gate pulse forming circuit 15 is connected to the input of the delay circuit 18 and to the output of the reflected ultrasonic vibrations preprocessing unit 5.

Figure 5B:
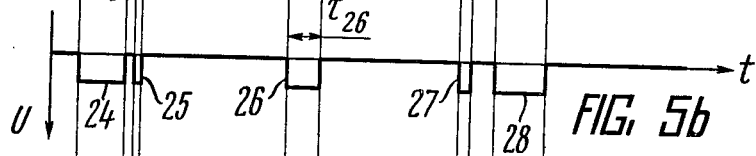
Figure 5C:
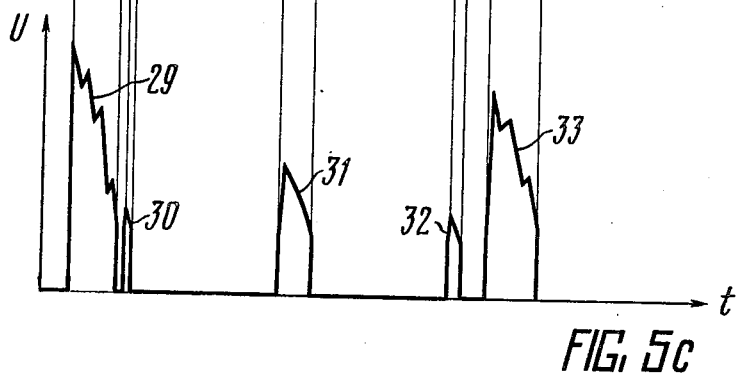

FIG. 5a is a time plot of voltage at the output of the no-noise-cutoff detector 7 (FIG. 1) in the form of pulse signals 19 (FIG. 5), 20, 21, 22 and 23 against the noise background with a maximum amplitude of noise voltage $U_o$ at a given portion;

FIG. 5b is a time plot of gate pulses 24, 25, 26, 27 and 28 of voltage at the output of the gate pulse forming circuit 15 (FIG. 1);

FIG. 5c is a time plot of voltage pulses 29 (FIG. 5), 30, 31, 32 and 33 at the output of the AND circuit 14 (FIG. 1).

The device for ultrasonic inspection of materials according to the invention operates as follows.

The synchronizer 2 (FIG. 1) actuates the sweep generator 12 and the ultrasonic generator 1. The latter actuates the ultrasonic converter 3 which converts electrical ultrasonic vibrations to mechanical vibrations which propagate in the material of the article 4 being tested, provided that there is acoustic contact between the surface of the ultrasonic converter 3 and that of the article 4.

Being reflected from the flaws 16 and the bottom surface 17 of the article 4 being tested, the elastic vibrations reach the ultrasonic converter 3 which converts them to electric signals against the noise background. These signals are applied via the reflected ultrasonic vibrations preprocessing unit 5 and the high-frequency amplifier 6 to the no-noise-cutoff detector 7.

Successively applied from the output of the no-noise-cut-off detector 7 to the inputs of the AND circuit 14 and the gate pulse forming circuit 15 are the pulse signal 19 (FIG. 5, plot a) of ultrasonic vibrations transmitted into the article 4 being tested, i.e. the main bang, as well as the pulse signals 20, 21 and 22 reflected from the flaws 16 (FIG. 1) of the article 4, and the pulse signal 23 (FIG. 5, plot a) reflected from the bottom surface 17 of the article 4. The pulse signals 19 (FIG. 5, plot a), 20, 21, 22 and 23 are received against the noise background and with a maximum amplitude of noise voltage $U_o$ at a given portion.

The gate pulse forming circuit 15 (FIG. 1) forms the gate pulses 24 (FIG. 5, plot b), 25, 26, 27 and 28 having durations $\tau_{24}$, $\tau_{25}$, $\tau_{26}$, $\tau_{27}$ and $\tau_{28}$, respectively, and time positions which correspond to the durations and time positions of the pulses 19 (FIG. 5, plot a), 20, 21, 22 and 23 at the output of the no-noise-cutoff detector 7 (FIG. 1).

The gate pulses 24 (FIG. 5, plot b), 25, 26, 27 and 28 thus formed are applied to the second input of the AND circuit 14 (FIG. 1) which carries out time selection of the pulse signals 19 (FIG. 5, plot a), 20, 21, 22 and 23, this being done within the time intervals $\tau_{24}$ (FIG. 5, plot b), $\tau_{25}$, $\tau_{26}$, $\tau_{27}$ and $\tau_{28}$ during which the amplitudes of the signals 19 (FIG. 5, plot a), 20, 21, 22 and 23 exceed the preset noise level $U_o$.

The amplitudes of the pulses 29 (FIG. 5, plot c), 30, 31, 32 and 33 thus selected (separated) are equal to the amplitudes of the initial pulse signals 19 (FIG. 5, plot a), 20, 21, 22 and 23, whereas their durations are equal to the durations of said initial pulse signals at a preset noise cutoff level $U_o$ which is equal to the trigger level of the gate pulse forming circuit 15 (FIG. 1).

By varying the trigger level of the gate pulse forming circuit 15, one can adjust the noise suppression level.

From the output of the AND circuit 14 (FIG. 1), the separated pulses 29 (FIG. 5, plot c), 30, 31, 32 and 33 are applied to the signals recording unit 9 and to the inputs of the video amplifier 10 and the automatic flaw signal indicator 11. From the output of the video amplifier 10, the video signals are applied to the vertical-deflection plates of the cathode ray tube 13; sweep voltage is applied to the horizontal-deflection plates of said cathode ray tube 13 from the output of the sweep generator 12. The sweep frequency and the ultrasonic vibrations frequency are set by the synchronizer 2.

The ratio of the amplitudes of the pulses 30 (FIG. 5, plot c), 31 and 32 reflected from the flaws 16 (FIG. 1) in the article 4 being tested, to the amplitude of the pulse 33 (FIG. 5, plot c) reflected from the bottom surface 17 (FIG. 1) of the article 4, or to the amplitude of the signal arriving from a reference reflector, is indicative of the dimensions of the flaws 16 detected during the test.

Operation of the device for ultrasonic inspection of materials, shown in FIG. 2, differs from that of the device of FIG. 1 in that the undetected electric signals against the noise background are directly applied from the output of the reflected ultrasonic vibrations preprocessing unit 5 (FIG. 1) to the input of the gate pulse forming circuit 15 and the first input of the AND circuit 14 of the unit 8 for separating signals from noise at a preset level, whereupon the time selection of these pulses is carried out.

From the output of the AND circuit 14, the undetected pulses, which are separated from the noise, are applied via the high-frequency amplifier 6 to the input of the no-noise-cutoff detector 7 from whose output the detected signals, separated from the noise, are applied to one of the inputs of the signals recording unit 9. In all other respects, operation of the device of FIG. 2 does not differ from that of FIG. 1.

In the device of FIG. 3, detected signals against the noise background are directly applied from the output of the no-noise-cutoff detector 7 to the input of the gate pulse forming circuit 15, whereas to the first input of the AND circuit 14 these signals are applied via the delay circuit 18 which is a wide-band delay line incorporating a high-frequency cable. The function of the delay circuit 18 may be performed by any other controlled wide-band delay line.

In all other respects, the device of FIG. 3 operates as the devices of FIGS. 1 and 2.

In the device of FIG. 4, signals against the noise background are applied from the output of the reflected ultrasonic vibrations preprocessing unit 5 to the input of the gate pulse forming circuit 15; to the first input of the AND circuit 14 these pulses are applied via the delay line 18 which, as in the case described above, is a wide-band delay line incorporating a high-frequency cable. In all other respects, operation of the device of FIG. 4 is like that described above.

The proposed method for ultrasonic inspection of materials and the device in accordance with the invention can be realized with the use of any known type of ultrasonic converter 3 (FIG. 1) such as direct, combined, slanted, or separated-combined converters, with the use of any known type of acoustic coupling between the ultrasonic converter 3 and the material of the article 4 being tested, such as contact, contact-immersion, immersion, or contactless coupling, as well as with the use of any known method for ultrasonic inspection of materials, whereby pulse signals are used as data carriers (these include the ultrasonic pulse-echo testing method, the through-transmission method, the resonance method, and the acoustic emission method).

The proposed method and device for ultrasonic inspection of materials can be realized with any known embodiment of the reflected ultrasonic vibrations preprocessing unit 5, the high-frequency amplifier 6, the no-noise-cutoff detector 7, the signals recording unit 9, the synchronizer 2 and the ultrasonic generator 1.

The method and device for ultrasonic inspection of materials in accordance with the invention can be applied to ultrasonic inspection of any materials (metals, alloys, non-metals, compositions) and joints (welded, glued, soldered and other types of joints), as well as in all cases where ultrasonic quality inspection of materials and products is normally resorted to.

The use of the proposed method for ultrasonic inspection of materials makes it possible to maintain the initial amplitudes of reflected signals, while completely cutting off noise at a preset level, the separation of signals from noise being effected by means of time selection of signals; this, in turn, makes it possible to make a correct quantitative evaluation of the dimensions of flaws 16 detected during a test without carrying out any additional operations.

The use of the proposed method accounts for a better sensitivity, which is due to the fact that the initial amplitudes of reflected signals are kept intact, while noise is cut off completely.

In addition, the keeping of the initial amplitude of signals intact, in the case of automatic ultrasonic inspection, makes it possible to evaluate the dimensions of flaws 16 without reducing the inspection efficiency.

The device for ultrasonic inspection of materials according to the invention is advantageous in that it maintains the dynamic range, although cutting off noise, which is due to the fact that the amplitude of signals separated from the noise are equal to the original amplitudes, and that the gain factor of the device's receiving channel remains unchanged.

Maintaining the absolute values of signals separated from the noise improves the effectiveness of automatic recording to the results of inspection.

The device of this invention is further advantageous in that it features a considerably improved resolution in both the longitudinal and transverse directions, which is due to the fact that the time selection of signals (the separation of signals from noise), effected with the aid of the gate pulse forming circuit 15 and the AND circuit 14, is accompanied by a reduction in the duration of the main bang 19 (FIG. 5, plot a) and the pulse signals 20, 21, 22 and 23 reflected from the flaws 16 (FIG. 1) and the bottom surface 17 of the article 4 being tested at zero level to a duration of these pulses at a preset level $U_o$ (FIG. 5, plot a) of cutting off noise. This feature comes in very handy in detecting flaws 16 (FIG. 1) close to the surface of the article 4 being tested.

The proposed device for ultrasonic inspection of materials accounts for a high confidence of inspection, which is due to the fact that the time selection of signals (the separation of signals from noise) is effected right after the preprocessing of reflected ultrasonic vibrations. This facilitates the subsequent amplification and processing of the signals.

The proposed device for ultrasonic inspection of materials features a high accuracy of time selection of signals (separation of signals from noise) due to the compensation of the time delay in the gate pulse forming circuit 15.

What is claimed is:

1. A method for ultrasonic inspection of materials, comprising the steps of
   transmitting ultrasonic vibrations into a material being tested;
   receiving and processing reflected ultrasonic vibrations;
   separating signals from noise at a preset level by means of time selection of these signals, performed within time intervals during which the amplitudes of said signals exceed said preset noise level;
   using said signals to evaluate the dimensions of flaws.

2. A device for ultrasonic inspection of materials, with time selection of signals (separating of signals from noise at a preset level and comprising:
   an ultrasonic generator;
   an ultrasonic converter acoustically coupled to a material being tested, its input being connected to an output of said ultrasonic generator;
   a reflected ultrasonic vibrations preprocessing unit whose input is connected to an output of said ultrasonic converter;
   a unit for separating signals from noise at a preset level;
   an AND circuit of said unit for separating signals from noise at a preset level;
   a gate pulse forming circuit of said unit for separating signals from noise at a preset level, an input of said gate pulse forming circuit being electrically coupled to a first input of said AND circuit, an output of said gate pulse forming circuit being connected to a second input of said AND circuit;
   a high-frequency amplifier whose input is connected to an output of said reflected ultrasonic vibrations preprocessing unit;
   no-noise-cutoff detector whose input is connected to an output of said high-frequency amplifier, whereas an output of said no-noise-cutoff detector is connected to said input of said gate pulse forming circuit;
   a signals recording unit whose first input is connected to an output of said AND circuit;
   a synchronizer whose first output is connected to an input of said ultrasonic generator, a second output of said synchronizer being connected to a second input of said signals recording unit.

3. A device for ultrasonic inspection of materials, employing time selection of signals (separation of signals from noise) at a preset level and comprising:
   an ultrasonic generator;
   an ultrasonic converter acoustically coupled to a material being tested, its input being connected to an output of said ultrasonic generator;
   a reflected ultrasonic vibrations preprocessing unit whose input is connected to an output of said ultrasonic converter;
   a unit for separating signals from noise at a preset level;
   an AND circuit of said unit for separating signals from noise at a preset level;
   a gate pulse forming circuit of said unit for separating signals from noise at a preset level, an input of said gate pulse forming circuit being electrically coupled to a first input of said AND circuit and connected to an output of said reflected ultrasonic vibrations preprocessing unit, whereas an output of said gate pulse forming circuit is connected to a second input of said AND circuit;
   a high-frequency amplifier whose input is connected to an output of said AND circuit;
   a no-noise-cutoff detector whose input is connected to an output of said high-frequency amplifier;
   a signals recording unit whose first input is connected to an output of said no-noise-cutoff detector;
   a synchronizer whose first output is connected to an input of said ultrasonic generator, whereas a second output of said synchronizer is connected to a second input of said signals recording unit.

4. A device as claimed in claim 2, including a delay circuit of said unit for separating signals from noise at a preset level, an input of said delay circuit being connected to said output of said no-noise-cutoff detector and to said input of said gate pulse forming circuit, whereas an output of said delay circuit is connected to said first input of said AND circuit.

5. A device as claimed in claim 3, including a delay circuit of said unit for separating signals from noise at a preset level, an input of said delay circuit being connected to said output of said reflected ultrasonic vibrations preprocessing unit and to said input of said gate pulse forming circuit, whereas an output of said delay circuit is connected to said first input of said AND circuit.

* * * * *